US009561326B2

(12) United States Patent
Cederschiöld et al.

(10) Patent No.: US 9,561,326 B2
(45) Date of Patent: Feb. 7, 2017

(54) COUPLING DEVICES AND KITS THEREOF

(75) Inventors: Alexander Cederschiöld, Göteborg (SE); Tobias Rosenquist, Kållered (SE)

(73) Assignee: Carmel Pharma AB, Gothenberg (SE)

( * ) Notice: Subject to any disclaimer, the term of this patent is extended or adjusted under 35 U.S.C. 154(b) by 784 days.

(21) Appl. No.: 13/367,622

(22) Filed: Feb. 7, 2012

(65) Prior Publication Data

US 2012/0203194 A1     Aug. 9, 2012

Related U.S. Application Data

(60) Provisional application No. 61/440,486, filed on Feb. 8, 2011.

(51) Int. Cl.
*A61B 19/00*    (2006.01)
*A61M 5/162*   (2006.01)
*A61J 1/14*      (2006.01)

(52) U.S. Cl.
CPC .............. *A61M 5/162* (2013.01); *A61J 1/14* (2013.01)

(58) Field of Classification Search
None
See application file for complete search history.

(56) References Cited

U.S. PATENT DOCUMENTS

| | | | | |
|---|---|---|---|---|
| 3,119,391 A | * | 1/1964 | Harrison | A61M 5/162 604/274 |
| 4,020,837 A | * | 5/1977 | Larson | A61J 1/2089 604/411 |
| 4,262,671 A | * | 4/1981 | Kersten | 604/251 |
| 4,787,898 A | * | 11/1988 | Raines | 604/411 |
| 4,857,068 A | * | 8/1989 | Kahn | 604/405 |
| 5,232,109 A | * | 8/1993 | Tirrell et al. | 215/247 |
| 6,409,708 B1 | * | 6/2002 | Wessman | 604/284 |
| 7,645,268 B2 | * | 1/2010 | Mickley | A61M 5/3286 604/274 |
| 2003/0191445 A1 | * | 10/2003 | Wallen et al. | 604/411 |
| 2007/0156112 A1 | * | 7/2007 | Walsh | 604/415 |
| 2008/0142388 A1 | * | 6/2008 | Whitley et al. | 206/438 |
| 2008/0172024 A1 | * | 7/2008 | Yow | 604/411 |
| 2010/0198158 A1 | * | 8/2010 | Loewen | 604/158 |
| 2010/0312220 A1 | | 12/2010 | Kalitzki | |

FOREIGN PATENT DOCUMENTS

| | | |
|---|---|---|
| CN | 101896215 A | 11/2010 |
| DE | 102007061346 | 6/2009 |
| GB | 2105695 | 3/1983 |
| WO | WO-03/086529 | 10/2003 |
| WO | WO-2004/004806 | 1/2004 |

OTHER PUBLICATIONS

PCT International Search Report and Written Opinion in PCT/US2012/024254, mailed Oct. 31, 2012, 16 pgs.
PCT International Preliminary Report on Patentability in PCT/US2012/024254, dated Aug. 13, 2013, 10 pages.

* cited by examiner

*Primary Examiner* — Bradley Philips
*Assistant Examiner* — Eric Bryant
(74) *Attorney, Agent, or Firm* — Servilla Whitney LLC (57) ABSTRACT

A coupling device for transferring substances, in particular medical substances, is disclosed. The coupling device can be used for transferring medical substances between a patient and an infusion bag containing the medical substances. In one or more embodiments, the coupling device may include a piercing member for connection to a medical device such as the infusion bag. A piercing member for a coupling device is also disclosed.

22 Claims, 7 Drawing Sheets

COUPLING DEVICES AND KITS THEREOF

CROSS-REFERENCE TO RELATED APPLICATIONS

This application claims priority under 35 U.S.C. §119(e) to U.S. Provisional Application No. 61/440,486, filed Feb. 8, 2011, the disclosures of which are incorporated herein by reference in their entirety.

TECHNICAL FIELD

The present invention relates to a coupling device for transferring substances, in particular medical substances. The coupling device can be used for transferring medical substances between a patient and an infusion bag containing the medical substances. The coupling device comprises a piercing member for connection to a medical device such as the infusion bag. The invention also relates to a piercing member for a coupling device.

BACKGROUND

Coupling devices are typically used for providing fluid ports to medical devices and used for transferring medical substances between, for example, devices such as containers and/or for drug administering from a container to a patient. An example of a use is the use of the coupling device together with an infusion bag, which in the following will be described for illuminating purposes.

Infusion bags are used for intravenous delivery of fluids and medically effective substances to human beings and animals. For this reason, the infusion bag is provided with an outlet through which fluid may flow to a component connected to the patient, such as a cannula or the like, and further into the body of the patient. When preparing the fluids which are to be administrated to the body from the infusion bag, a usual method is that medically effective substances are supplied to a pre-sealed infusion bag which is filled with a transport fluid, such as a sodium chloride solution or a glucose solution. The preparation is performed by injecting the medically effective substance via an inlet into the bag.

For accomplishing the desired transferring of fluid a combined inlet and outlet of the infusion bag together with the coupling device which is denoted "injection spike" or just "spike" are often used.

The spike has a needle-formed piercing member by means of which a bather, membrane or septum arranged in a narrow passage of the infusion bag, constituting inlet/outlet of the infusion bag, may be penetrated so that the infusion bag may be opened towards two channels arranged in the spike when the spike is introduced in the inlet/outlet of the infusion bag. One of the channels is intended for conveyance of fluid in a direction from the infusion bag towards the patient and the other channel is intended for injection of medical substances into the infusion bag. In the other end of the spike are members arranged at the mouths of the channels for connection to other components, such as flexible tubes for conveyance of the fluid further to the patient and cannulas for the injection of medical substances to the infusion bag.

WO 2004/004806 A1 discloses such a spike for transferring medical substances and fluids to and from infusion bags.

WO2003/086529 discloses a device for mixing medical fluids and for introducing substances into an infusions system. The device is composed of two portions. The first portion is made of a thermoplastic material, such as polypropylene (PP), polycarbonate (PC) or Acrylonitrile butadiene styrene polymer (ABS polymer). The second portion is made of an elastomeric polymer material or a synthetic rubber material.

In view of the known coupling devices, there is a need to provide an improved and/or alternative coupling device, which provides a fluid port to medical devices, while being easy and safe to use for a long-term period.

SUMMARY

A first aspect of the present invention pertains to a coupling device that provides a first medical device with a fluid port. In one or more embodiments, the coupling device may include at least one connection site that receives and connects a second medical device, a piercing member having a longitudinal axis A, a piercing tip portion and a piercing tip, the piercing member being arranged in fluid communication with the at least one connection site and adapted to pierce a membrane on the first medical device that provides the first medical device with the fluid port. In one or more embodiments, the piercing member may include a first fluid channel and a second fluid channel, the first fluid channel and second fluid channels having a first opening at the piercing tip portion.

In one or more embodiments, the first fluid channel and second fluid channels are separated by a fluid channel separation wall, the fluid channel wall having a convex surface portion, with respect to the longitudinal axis A, the convex surface portion faces the first fluid channel at the piercing tip portion.

In one or more embodiments, the convex surface portion of the coupling device may extend the full length between the fluid channel separation wall.

In one or more embodiments, the fluid channel wall of the coupling device may include a concave portion, with respect to a longitudinal axis the concave portion facing the second fluid channel at the piercing tip portion. In one or more embodiments, the concave surface portion may extend the full length of the fluid channel separation wall.

In one or more embodiments, the convex surface portion of the fluid channel separation wall projects from the first opening of the first channel so as to form the piercing tip.

In one or more embodiments, the first fluid channel of the coupling device may include a fluid channel separation wall and an opposing first outer wall, and in that the second fluid channel is defined by the fluid channel separation wall and an opposing second outer wall.

In one or more embodiments, the first opening of the first fluid channel may include a first cut surface having a rim on the opposing first outer wall, and the first opening of the second fluid channel may include a second cut surface defined by a rim of the opposing second outer wall. The first and second cut surfaces are adapted to pierce the membrane. In one or more embodiments, the first and second cut surfaces of the opposing first and a second outer walls are arranged at separate distances from the piercing tip of the piercing member and with respect to the longitudinal axis A.

In one or more embodiments, the first and second cut surfaces of the opposing first and a second outer walls are separated by a distance so that the second cut surface of the opposing second outer wall is exposed to the membrane before the first cut surface of the opposing first outer wall during piercing of the membrane.

In one or more embodiments, the convex surface portion of the fluid channel separation wall is arranged to be inserted and displaced in the membrane before the first cut surface of the opposing first outer wall is introduced into the membrane.

In one or more embodiments, the convex surface portion of the fluid channel wall projects from the first opening of the first fluid channel a distance of about 3-15 mm.

In one or more embodiments, the convex surface portion of the fluid channel wall projects a distance between the first cut surface of the opposing first outer wall and the piercing tip.

In one or more embodiments, the first fluid channel has an arc shaped cross section. In one or more embodiments, the second fluid channel has a circular cross section.

In one or more embodiments, the coupling device may include a second connection site adapted to receive and connect to a hose or tube.

In one or more embodiments, the piercing member of the coupling device may include polypropylene, high-density polyethylene, polytetrafluoroethylene, or mixtures thereof. In one or more embodiments, the polypropylene is a homopolypropylene. In one or more embodiments, at least one polymer has a tensile modulus of 1200-2500 MPa as measured by a method according to ISO 527.

In one or more embodiments, the piercing member is manufactured from a first polymer composition and the at least one connection site is manufactured from a second polymer composition, different from the first polymer composition.

In one or more embodiments, the first fluid channel of the coupling device has a first cross section in plane B-B and in that the second fluid channel has a second cross section in plane B-B, wherein the first cross section of the first fluid channel is different from the second cross section of the second fluid channel.

In one or more embodiments, the first cross section in plane B-B of the first fluid channel is substantially arc formed. In one or more embodiments, the second cross section in plane B-B of the second fluid channel is substantially circularly formed.

A second aspect of the present invention pertains to a coupling device for providing a first medical device with a fluid port. In one or more embodiments, the medical device may be an infusion bag. The coupling device may include at least one connection site adapted to receive and connect a second medical device, a piercing member having a longitudinal axis A, a piercing tip portion and a piercing tip. In one or more embodiments, the piercing member being arranged in fluid communication with the at least one connection site and adapted to pierce a membrane on the first medical device to thereby provide the medical device with the fluid port. In one or more embodiments, the piercing member may include a first and a second fluid channel. In one or more embodiments, the first and second fluid channels may include a first opening at the piercing tip portion, wherein the first opening of the first fluid channel is further distanced from the tip, than the first opening of the second fluid channel, thus enabling the first opening of first fluid channel to enter the membrane after the second opening of the second fluid channel has entered the membrane.

A third aspect of the present invention pertains to a kit including the coupling device of and an infusion bag.

In the following, a more detailed description of embodiments will now be given with reference to drawings.

BRIEF DESCRIPTION OF THE DRAWINGS

FIG. 1b is a schematic sectional side view through the device in FIG. 1a.

DETAILED DESCRIPTION

Figure 1:
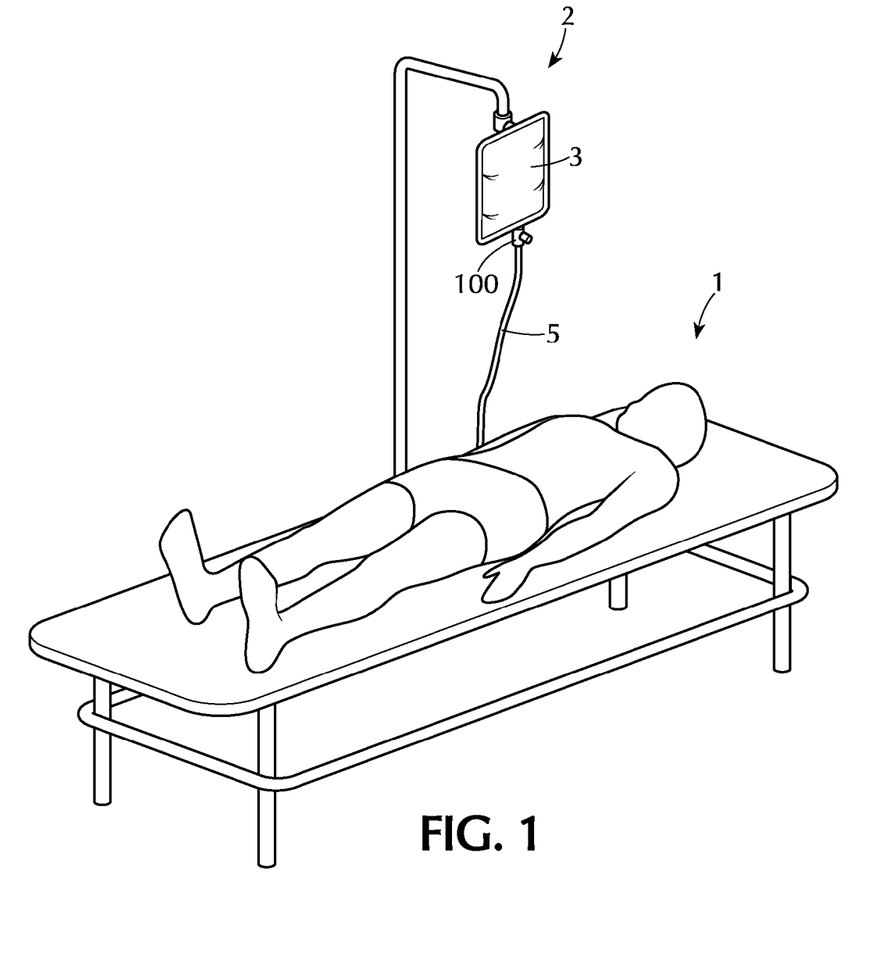
FIG. 1 shows a patient that is being administrated with infusion from a medicament administration system.

FIG. 1 shows a patient 1 that is being administrated with IV infusion from a medicament administration system 2 comprising a first fluid container 3 provided with a coupling device 100, in the form of an infusion spike. The coupling device 100 is connected to a hose 5, in fluid communication with the blood circulation system of the patient 1, a piercing member (not shown), forced into the first fluid container 3, and a connection site, into which medicine can be administrated by means of a fluid injector such as a syringe (not shown).

Figure 1A:
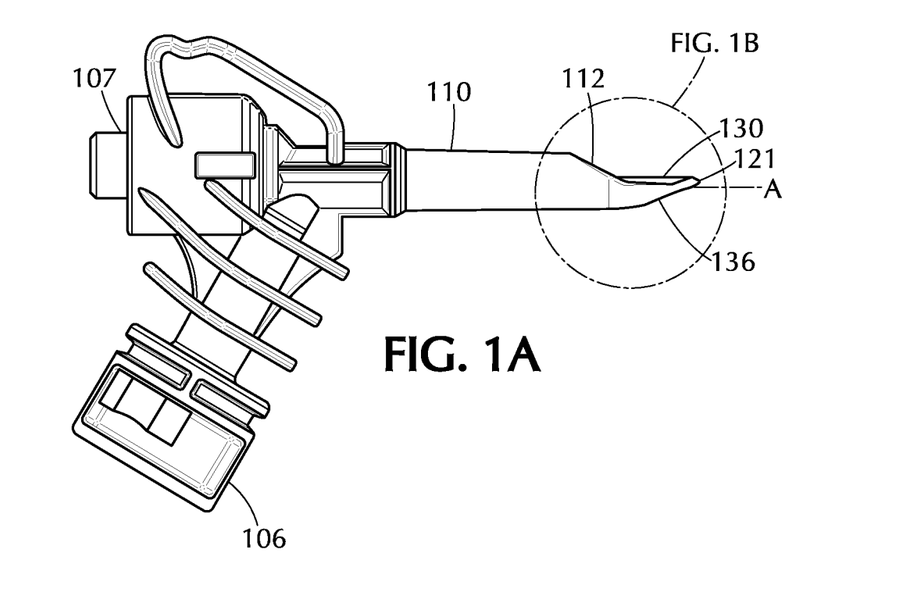
FIG. 1a is a schematic side view of a coupling device according to one embodiment.

FIG. 1a shows the coupling device 100 according to an embodiment of the present invention, wherein the coupling device is in the form of an infusion spike 101. The coupling device 100 will be described in greater detail hereafter with reference to FIGS. 1a-2e. The coupling device 100 comprises a first connection site 106, a second connection site 107 and a piercing member 110.

Figure 1B:
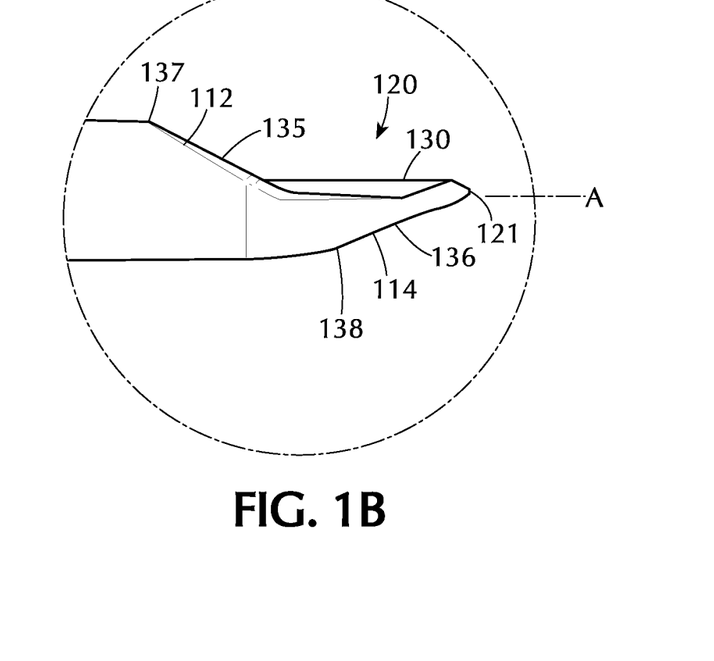

In FIG. 1b, a cross section of the coupling device from FIG. 1a is shown. The piercing member 110 comprises a first fluid channel 111 with a first opening 112, and a second fluid channel 113 with a first opening 114. The piercing member extends along a longitudinal axis A. The first fluid channel 111 is in fluid communication with a first connection site adapted to connect a hose or similar while the second fluid channel is in fluid communication with a second connection site for connecting a medical device for example. The first and the second fluid channels 111, 113 leads to a piercing tip portion 120 having a piercing tip 121, or just referred to as the tip 121.

The first and the second fluid channels 111, 113 are separated by a fluid channel separation wall, hereafter referred to only as the separation wall 130. As seen in FIG. 1a, the separation wall projects from the first opening 112 of the first fluid channel at the piercing tip portion 120, and form the tip 121 of the piercing member. In FIG. 1b, the separation wall 130 has two opposing walls 131, 132. The opposing first wall 131 forms together with the separation wall the first fluid channel 111, while the opposing second wall 132 forms the second together with the separation wall 130 the second fluid channel 113.

Figure 2:
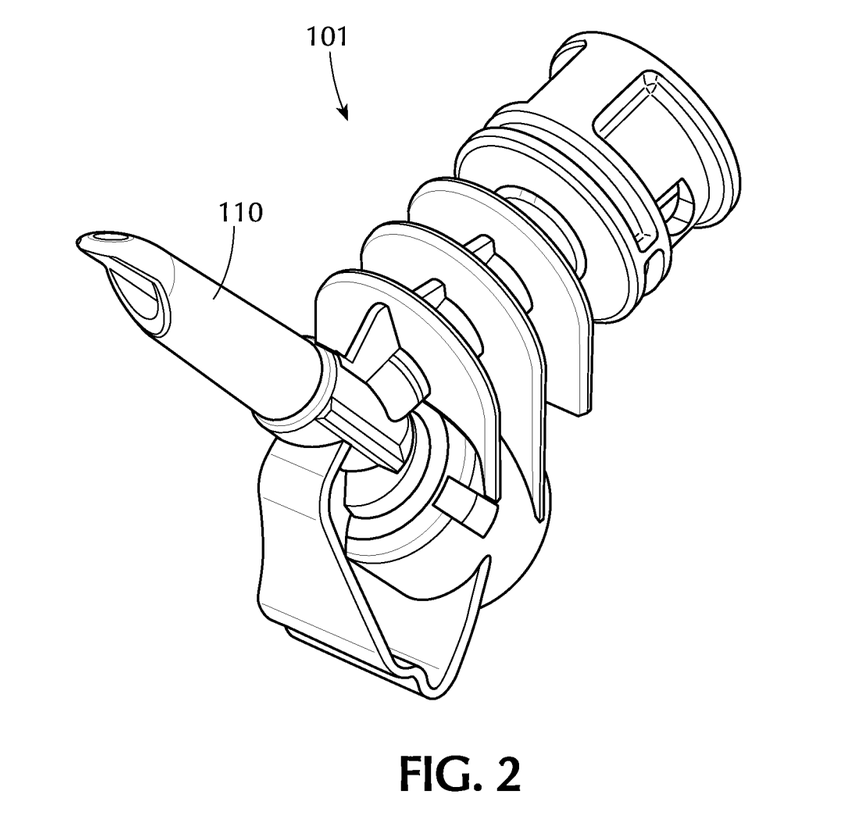
FIG. 2 is a schematic perspective view of a coupling device according to one embodiment.

FIG. 2 illustrates one embodiment of the coupling device of the present invention, i.e. an infusion spike 101, which is provided with a needle-formed piercing member 110 which may be introducible in a part which constitutes an inlet/outlet of a medical device such as an infusion bag (not illustrated). This inlet/outlet part of the infusion bag may be designed as a flexible tube with a circular cross-section corresponding to the cross-section of the piercing member 110 of the coupling device 100 and may have, before the introduction of the piercing member 110, a membrane, e.g.

a sealing membrane, arranged at a mouth. The injection spike is provided with two fluid channels for fluid connection between a piercing tip portion and a connection site for a hose or the like and a site for connection to, for example, a fluid injector such as a syringe. The arrangement will be described in more detail below. During the introduction of the spike 101, the piercing member 110 penetrates the membrane and the infusion bag be opened towards channels in the spike 101. A fluid port is thus provided on the infusion bag.

Figure 2A:
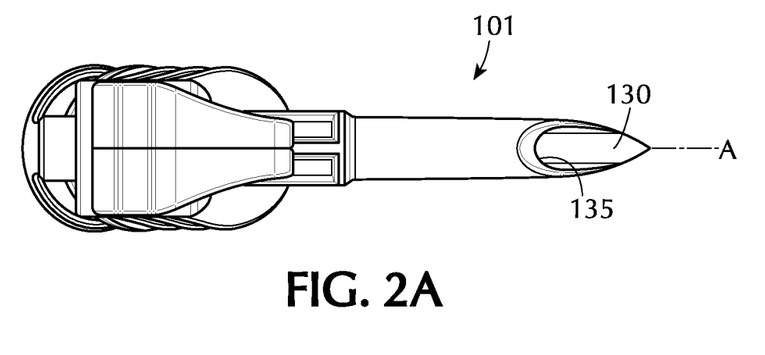
FIG. 2a is a schematic view of a coupling device seen from above

In FIG. 2a, coupling device 100, and the projecting separation wall 130 is seen from above. As is noticed, the separation wall is clearly visible as it has an exposed area outside of the first fluid channel. The exposed area can be between 1-10 mm2, when seen from above as illustrated in FIG. 2a. A rim 135 forms the opening 112 of the first fluid channel 111 and also provides for a cut surface. The cut surface assists in providing a good and clean penetration through the membrane during penetration thereof. The second fluid channel 113 is provided with a rim 136 forming the opening 114 of the second fluid channel 113 which also provides for a cut surface.

Figure 2B:
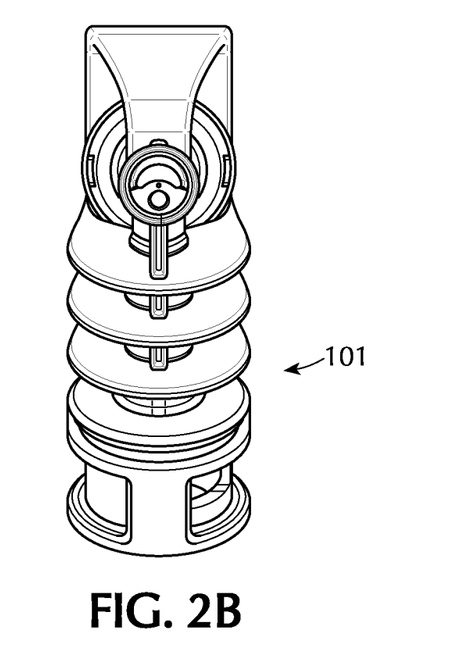
FIGS. 2b-2e are schematic views of a coupling device as seen from the top, below, side, and cross-section.
Figure 2C:
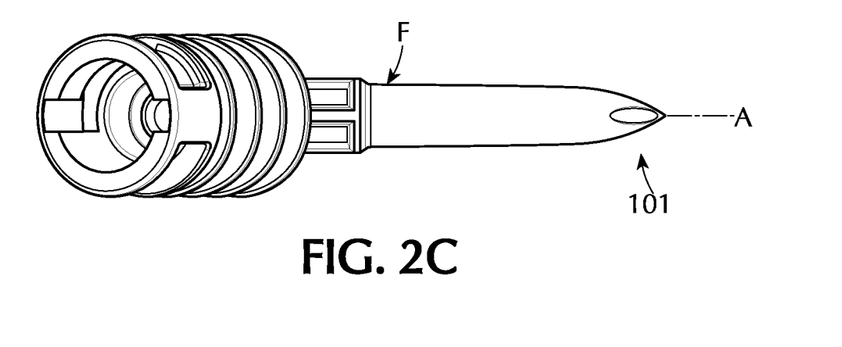
Figure 2D:
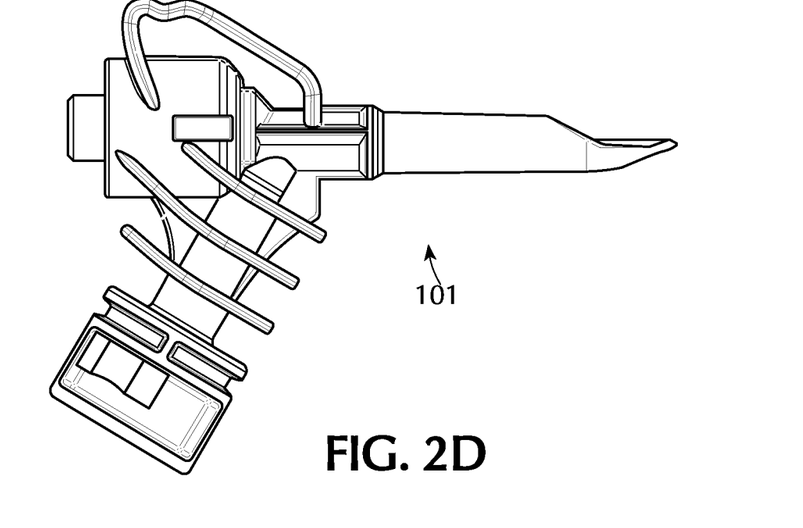

FIGS. 2b-2c illustrates the coupling device as seen from the top, below and side.

Figure 2E:
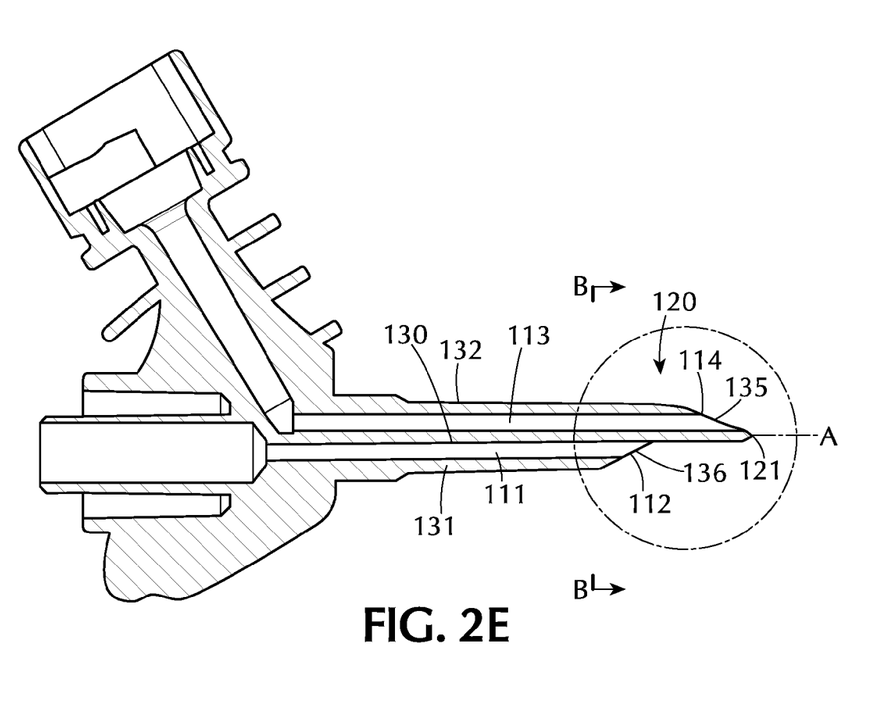
Figure 3A:
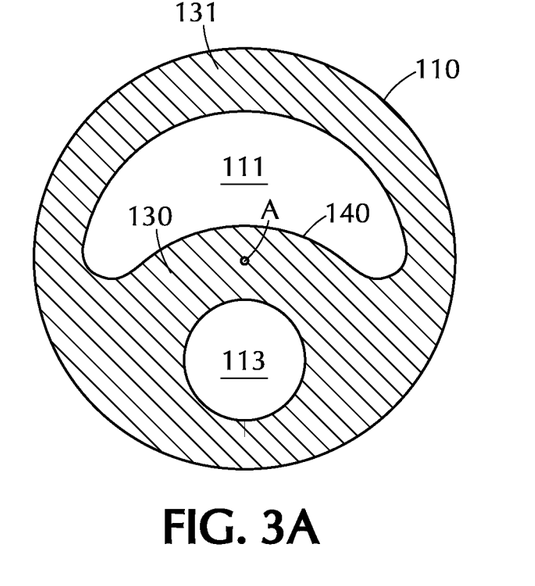
FIG. 3a is a sectional top view of plane B-B in a piercing member part of the coupling device in FIG. 1b.
Figure 3B:
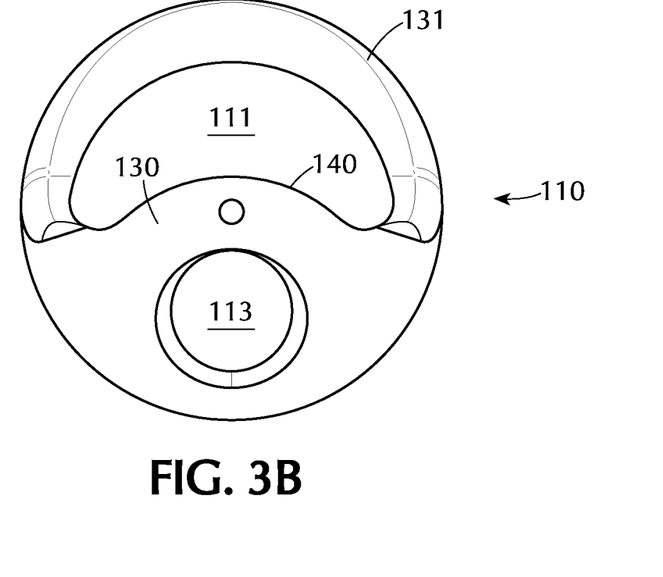
FIG. 3b is a top view of a piercing tip portion of a piercing member.

In FIGS. 1a, 2e and 3b, the enlargement of the piercing tip portion can be seen. As is noticed, the cut surfaces, i.e. the rims 135, 136, of the first and the second fluid channels are displaced with respect to the longitudinal axis A. Hence they have different distances to the tip 121 of the piercing member 110 as measured along the longitudinal axis A. This enables a good penetration property for the piercing member. As can be noticed, the rim 135 has a crest 137, the distance of the crest 137 of the rim 135 of the first fluid channel 111 to the tip is about 10 mm, and between 6-15 mm is suitable, 7-13 mm preferable. The rim 135 of the first fluid channel further transcends to the separation wall, rather than transcends to a tip, and the separation wall 130 instead form the tip.

Furthermore, the outer portion of the piercing member 110 is also provided with portions tapering in a direction towards an end of the piercing tip 121. This provides easy insertion through membranes or bathers, for example.

While for the crest 138 of the rim 136 of the second fluid channel, the distance is only 5 mm, 3-5 mm is suitable. The rim 136 of the second fluid channel 113 substantially transcends to the tip 121. In practice, this means that the whole rim 136 of the second fluid channel 113 is introduced into the membrane before the rim 135 of the first fluid channel 111 is introduced into the membrane. The openings 112, 114 of the first and second fluid channels 111, 113 are thus introduced separately into the membrane during penetration. This provides for a good and clean penetration which reduces the risk for small membrane chips to accidentally be torn off from the membrane during penetration.

However, the piercing member should also be rigid enough so that the piercing member does not bend during penetration of the membrane. The separation wall 130 is provided with a convex surface 140 defining a part of the first fluid channel 111 with respect to the longitudinal axis A. The convex surface can extend the full length of the first fluid channel 111, 50-100% of the length of the first fluid channel 111 is advantageous. The opposing first outer wall 131 and the opposing second outer wall 132 are visible.

FIGS. 3a-b illustrates an embodiment of channel arrangement and cross-sectionals shapes of the channels. According to the embodiment, the first channel may at least in a portion along the channel adopt a circular cross-sectional shape, while the second channel may adopt a different shape, in this case an arc form or a crescent or banana shape.

FIG. 3a shows a cross section in the plane B-B as illustrated in FIG. 1a. FIG. 3a shows the first fluid channel 111, and the second fluid channel 113 separated by the separation wall 130. As is noted, the cross section of the first fluid channel 111 is substantially arc formed while the cross section of the second fluid channel 113 is circular. The convex surface can be described as a surface having a radius curvature of 1-5 mm, or 1-3 mm or 1-2 mm. The opposing first outer wall can have a radius of 1-5 mm. The radius is from the piercing tip 121 continuously increasing along the channel 111. The radius of the convex surface at the piercing tip 121 may be around 10 percent smaller than the radius at the base indicated in FIG. 2c with arrow F.

Different cross sections are possible, for example the piercing member can have two or more fluid channels, three or more, optionally four or more fluid channels.

The cross section area of the first fluid channels is twice as large as the cross section area of the second fluid channel, the ratio can however be 1,5-4 (cross section area of the first fluid channel/cross section area of the second fluid channel). Thus there is enabled a higher volume flow in the first fluid channel 111 as compared with the second fluid channel 113.

The longitudinal axis A is the center axis of the piercing member 110.

According to one embodiment the coupling device 100 may comprise a material selected from the group consisting of polypropylene (PP), homopolypropylene, high-density polyethylene (HDPE) and polytetrafluoroethylene (PTFE) mixtures thereof.

Such a material provides the possibility of providing stiffness to the coupling device 100 and its piercing member 110, which allows the piercing member 110 to penetrate a membrane or barrier in a vessel in an intact form. Furthermore, the material provides a possibility of withstanding substances used in connection with medical device systems in which the coupling device 100 may be used. Example of such substances are polyethylene glycol, dimethylacetamide, and alcohols.

According to an embodiment, at least said piercing member 110 comprises the selected material.

According to an embodiment, the coupling device 100 is manufactured from at least one polymer selected from the mentioned polymer material.

According to an embodiment, the piercing member 110 is manufactured from a first polymer composition and the at least one connection site is manufactured from a second polymer composition, different from the first polymer composition.

The PP may be of a homopolymer type. At least the piercing member 110 is manufactured from homopolypropylene. Properties related to listed sample polymers are provided in Table 1.

TABLE 1

Physical Properties of the Polymers.

| | Unit | Test Method | Sample No. 1 | Sample No. 2 | Sample No. 3 | Sample No. 4 | Sample No. 5 | Sample No. 6 | Sample No. 7 |
|---|---|---|---|---|---|---|---|---|---|
| Polymer | | | PP homo | PP | PP homo | PP homo | PP homo | PP homo | PP homo |
| Density | (g/cm$^3$) | ISO 1183 | 0.91 | 0.907 | 0.9 | 0.9 | 0.9 | | |
| Mould Shrinkage | (%) | ISO 294 | — | 1-2 | | | | | |
| Melt Flow Rate | (g/10 min) | ISO 1133 | 8 | 10 | 23 | 7.5 | 60 | 3 | 12 |
| Flexural Modulus | (MPa) | ISO 178 | — | | | | 1550 | 1450 | 1400 |
| Tensile Modulus | (MPa) | ISO 527 | 1800 | 1100 | 1500 | 1400 | 1700 | | |
| Tensile Stress at Yield | (MPa) | ISO 527 | 38 | 29.5 | 34 | 31 | 33 | 35 | 34 |
| Tensile Strain at Yield | (%) | ISO 527 | 7.5 | 13 | 8 | 10 | 9 | | |
| Charpy Nothed Impact Strength at 23° C. | Kj/m$^2$ | ISO179 1eA | 5.5 | 4.5 | 2.5 | 3.5 | 3 | | 3 |

The material selected should provide stiffness property to the coupling device 100 and its piercing member 110, which allows the piercing member 110 to penetrate a membrane of a vessel, or vial, without bending or breaking. The required criteria regarding penetration of a membrane and examples of suitable materials are shown in Table 1.

In the following, some embodiments of polymer parameters for providing the certain stiffness are given.

According to an embodiment, the selected polymer may have a tensile modulus according to ISO 527 of 1000-2500 MPa.

According to an embodiment, the tensile modulus may be 2200 MPa or less, 2000 MPa or less, or 1900 MPa or less.

According to an embodiment, the tensile modulus may be 1000 MPa or more, 1100 MPa or more, 1200 MPa or more, 1300 MPa or more, 1400 MPa or more, 1500 MPa or more, or 1700 MPa or more.

According to an embodiment, the tensile modulus may be 1400-2500 MPa, 1400-1800 MPa or 1850-1950 MPa.

According to an embodiment, the tensile modulus may be around 1800 MPa.

According to an embodiment, the selected polymer may have a tensile stress at yield according to ISO 527 of 28-40 MPa.

According to an embodiment, the tensile stress may be 40 MPa or less, or 38 MPa or less.

According to an embodiment, the tensile stress may be 28 MPa or more, or 30 MPa or more, or 31 MPa or more.

According to an embodiment, the selected polymer may have a tensile strain at yield according to ISO 527 of 5-15 MPa.

According to an embodiment, the tensile strain may be 15% or less, 13% or less or 11% or less.

According to an embodiment, the tensile strain may be 5% or more, or 6% or more, or 7% or more.

The coupling device 100 may comprise polytetrafluoroethylene. According to an embodiment, at least the material or materials used in coupling device 100 parts which are in contact with fluids and/or chemical substances during use should be resistant enough to the fluids and/or chemical substances so that the material provides the piercing functionality of the piercing member during use. In the examples below it indicated that the mentioned materials such as PP would be acceptable.

According to one embodiment, at least the surfaces of the channels and the piercing member 110 are coated with polytetrafluoroethylene.

According to an embodiment, the coupling device 100 material may at least in part be coated with PP, homopolypropylene or high-density propylene, or polytetrafluoroethylene (PTFE; also known by the trade mark Teflon). The person skilled in the art will understand how to apply such a coating.

This provides the possibility of providing better chemical resistance against chemicals used in the solutions that are in contact with the coupling device 100 during use. The coupling device 100 materials to be coated may be selected from the group consisting of plastics such as PP, HDPE, polycarbonate (PC) or ABS polymer, or a combination thereof. The coating may be arranged on any portion that is in contact with solutions during use, such as the channel wall surfaces and an outer surface of the piercing member 110.

Different parts of the coupling device 100 may be of different materials. According to one embodiment, at least the piercing member 110 comprises or consists of the material or combinations of materials mentioned above, and may optionally be in part or fully are coated with PTFE.

According to another embodiment the whole coupling device 100 is made of the same material or combination of materials and may optionally be in part or fully be coated with PTFE.

In the foregoing description and the following examples, the present invention has been described in connection with a few specific embodiments and with reference to the attached drawings and examples.

However, the present invention is by no means strictly confined to these embodiments or to what is shown in the drawings and examples.

The coupling device 100 is described further through the non-limiting recital of examples. In these examples the aspects of different materials for use in a coupling device are given.

Material

The material selected can provide stiffness to the coupling device and its piercing member, which allows the piercing member 110 to penetrate a membrane in a vessel in an intact form. The required criteria regarding penetration of a membrane are defined in a method based on ISO 8871.

In Table 1, several PP materials with the required stiffness are given. All material (samples 1-7) were shown to provide rigidity (stiffness) to a coupling device for penetrating the membrane. Nevertheless, according to further embodiments as mentioned above, the material may be selected from PP materials with an increased stiffness as compared to polymer sample 2. From Table 1, it is shown that materials selected from PP of homopolymer types have increased stiffness as compared to sample 2, and these materials thus provides good piercing capabilities to a piercing member, in particular sample 1.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

The invention claimed is:

1. A coupling device that provides a first medical device with a fluid port, said coupling device comprising
at least one connection site that receives and connects a second medical device,
a piercing member having a longitudinal axis A, a piercing tip portion and a piercing tip, said piercing member being arranged in fluid communication with said at least one connection site and adapted to pierce a membrane on said first medical device that provides said first medical device with said fluid port, an outer portion of the piercing member being tapered in a direction towards an end of the piercing tip;
said piercing member comprises a first fluid channel and a second fluid channel, said first fluid channel and said second fluid channel having a first opening at said piercing tip portion, wherein said first opening of said first fluid channel has a first cut surface having a rim on an opposing first outer wall, and said first opening of said second fluid channel has a second cut surface defined by a rim of an opposing second outer wall, the rim of the first fluid channel transcends to a separation wall and the rim of the second fluid channel transcends to the piercing tip;
wherein said first fluid channel and said second fluid channel are separated by a fluid channel separation wall, said fluid channel separation wall having a convex surface portion, with respect to said longitudinal axis A, said convex surface portion faces said first fluid channel at said piercing tip portion wherein said first fluid channel separation wall further comprises a concave portion, with respect to said longitudinal axis A, said concave portion facing said second fluid channel at said piercing tip portion, wherein said concave portion extends fully along said fluid channel separation wall;
wherein a distance of a crest of the rim of the first fluid channel to the piercing tip is between 6-15 mm and a distance of a crest of the rim of the second fluid channel to the piercing tip is between 3-5 mm, wherein said first fluid channel has a cross-sectional area twice as large as the cross-sectional area of the second fluid channel.

2. The coupling device of claim 1, wherein said convex surface portion extends fully along said fluid channel separation wall.

3. The coupling device of claim 1, wherein at said piercing tip portion, said convex surface portion of said fluid channel separation wall projects from said first opening of said first channel so as to form said piercing tip.

4. The coupling device of claim 1, wherein the first fluid channel is defined by said fluid channel separation wall and an opposing first outer wall, and in that said second fluid channel is defined by said fluid channel separation wall and an opposing second outer wall.

5. The coupling device of claim 4, said first and second cut surfaces are adapted to pierce said membrane.

6. The coupling device of claim 5, wherein said first cut surface and said second cut surface of said opposing first outer wall and a second outer wall are arranged at separate distances from said piercing tip of said piercing member and with respect to said longitudinal axis A.

7. The coupling device of claim 6, and said first cut surface and said second cut surface of said opposing first outer wall and a second outer wall are separated by a distance so that said second cut surface of said opposing second outer wall is exposed to said membrane before said first cut surface of said opposing first outer wall during piercing of said membrane.

8. The coupling device of claim 5, wherein said convex surface portion of said fluid channel separation wall is arranged to be inserted and displaced in said membrane before said first cut surface of said opposing first outer wall is introduced into said membrane.

9. The coupling device of claim 1, wherein said convex surface portion of said fluid channel separation wall projects from said first opening of said first fluid channel a distance in a range of 3-15 mm.

10. The coupling device of claim 5, wherein said convex surface portion of said fluid channel wall projects a distance between said first cut surface of said opposing first outer wall and said piercing tip.

11. The coupling device of claim 1, wherein said first fluid channel has an arc shaped cross section.

12. The coupling device of claim 1, wherein said second fluid channel has a circular cross section.

13. The coupling device of claim 1, wherein said coupling device comprises a second connection site adapted to receive and connect to a hose or tube.

14. The coupling device of claim 1, wherein at least said piercing member comprises polypropylene, high-density polyethylene, polytetrafluoroethylene, or mixtures thereof.

15. The coupling device of claim 14, wherein the polypropylene is a homopolypropylene.

16. The coupling device of claim 14, wherein said piercing member is manufactured from a first polymer composition and said at least one connection site is manufactured from a second polymer composition, different from said first polymer composition.

17. The coupling device of claim 16, wherein the at least one polymer has a tensile modulus of 1200-2500 MPa as measured by a method according to ISO 527.

18. The coupling device of claim 16, wherein said first fluid channel has a first cross section in plane B-B and in that said second fluid channel has a second cross section in plane B-B, wherein said first cross section of said first fluid channel is different from said second cross section of said second fluid channel.

19. The coupling device of claim 18, wherein said first cross section in plane B-B of said first fluid channel is arc formed.

20. The coupling device of claim 19, wherein said second cross section in plane B-B of said second fluid channel is circularly formed.

21. A kit comprising the coupling device of claim 1 and an infusion bag.

22. A coupling device for providing a first medical device with a fluid port, said coupling device comprising
at least one connection site adapted to receive and connect a second medical device,
a piercing member having a longitudinal axis A, a piercing tip portion and a piercing tip, said piercing member being arranged in fluid communication with said at least one connection site and adapted to pierce a membrane on said first medical device to thereby provide said first medical device with said fluid port,
said piercing member comprises a first fluid channel and a second fluid channel, said first fluid channel and said second fluid channel each having a first opening at said piercing tip portion, wherein said first fluid channel and said second fluid channel are separated by a fluid channel separation wall, said fluid channel separation wall having a convex surface portion, with respect to said longitudinal axis A, said convex surface portion faces said first fluid channel at said piercing tip portion, wherein said first opening of said first fluid channel has a first cut surface having a rim on an opposing first outer wall, and said first opening of said second fluid channel has a second cut surface defined by a rim of an opposing second outer wall, the rim of the first fluid channel transcends to a separation wall and the rim of the second fluid channel transcends to the piercing tip, wherein said first opening of said first fluid channel is further distanced from said piercing tip, than said first opening of said second fluid channel, thus enabling the first opening of said first fluid channel to enter said membrane after said second opening of said second fluid channel has entered said membrane, and wherein a distance of a crest of the rim of the first liquid channel to the piercing tip is between 6-15 mm and a distance of a crest of the rim of the second liquid channel to the piercing tip is between 3-5 mm, wherein said first fluid channel has a cross-sectional area twice as large as the cross-sectional area of the second fluid channel.

* * * * *